United States Patent [19]
Vann et al.

[11] 3,975,511
[45] Aug. 17, 1976

[54] SOLID PHASE RADIOIMMUNOASSAY

[75] Inventors: William P. Vann, Beaver Dams; Sidney Yaverbaum, Big Flats, both of N.Y.

[73] Assignee: Corning Glass Works, Corning, N.Y.

[22] Filed: Mar. 1, 1974

[21] Appl. No.: 447,252

[52] U.S. Cl. ............................. 424/1.5; 23/230 B; 250/303; 424/12
[51] Int. Cl.² ..................... G01N 33/00; G01T 1/16; G21H 5/02
[58] Field of Search ................... 23/230 B; 250/303; 424/1, 12

[56] References Cited
UNITED STATES PATENTS

| | | | |
|---|---|---|---|
| 3,519,538 | 7/1970 | Messing et al. | 424/12 |
| 3,652,761 | 3/1972 | Woetall | 424/12 |
| 3,669,841 | 6/1972 | Miller | 195/63 |

*Primary Examiner*—Benjamin R. Padgett
*Assistant Examiner*—Christine M. Nucker
*Attorney, Agent, or Firm*—James A. Giblin; Clinton S. Janes, Jr.; Clarence R. Patty, Jr.

[57] ABSTRACT

Method of determining the concentration of a substance in a solution which comprises the steps of incubating the solution with a known amount of radioactively labelled substance and a suspendable composite consisting of anti-substance antibody coupled chemically through an intermediate silane coupling agent to an inorganic carrier, the incubation period being for a time sufficient to form immunochemical complexes, separating the complexes from the solution, determining the radioactivity of either the separated complexes or the remaining solution, and relating that determination to a standard curve. Specific assays for digoxin, insulin, and estriol are disclosed.

9 Claims, 5 Drawing Figures

SOLID PHASE RADIOIMMUNOASSAY

BACKGROUND OF THE INVENTION

1. Field

This invention relates generally to the field of radioimmunoassay and specifically to solid-phase radioimmunoassay.

Radioimmunoassay (RIA) is a term used to describe any of several methods for determining very small concentrations of substances (especially in biological fluids), which methods are based on the use of radioactively labelled substances which can form immunochemical complexes with antibodies to that substance. Various RIA techniques are known for measuring concentrations of both antibodies and substances for which there exist antibodies. The RIA of a substance for which there exists antibodies (specific to that substance) is based on the observation that a known amount of that substance which has been radioactively labelled will tend to compete equally with an unknown amount of that substance (unlabelled) for a limited number of complexing sites on antibodies specific to the substance. Thus, a RIA of a given substance is performed as follows: a known amount of labelled substance and the unknown amount of that substance (unlabelled) are incubated with antibodies specific to the substance. During incubation, immunochemical complexes of both antibody-substance (labelled) and antibody-substance (unlabelled) are formed. The complexes are then removed from the incubation solution. Radioactivity counts are then taken of either the removed complexes or the remaining solution. The counts can be used to determine the unknown concentration by relating the counts to standard curves prepared beforehand using constant known amounts of labelled substance and known amounts of unlabelled substance.

An essential step in RIA methods in the separation of complexed products from the incubation solution. Ideally, the separation should be relatively simple and quick. It has been recognized that separation is greatly facilitated by using antibodies which have been immobilized by attachment to essentially water-insoluble carrier materials. When such carrier materials are used in RIA, the technique is commonly referred to as solid phase RIA, or SPRIA.

2. Prior Art:

Antibodies, antigenic substances, and other substances such as enzymes have been attached by covalent bonds to various organic substances as shown by U.S. Pat. No. 3,555,143 (proteins), issued to Axen et al. on Jan. 12, 1971, U.S. Pat. No. 3,645,852 (proteins), issued to Axen et al. on February 29, 1972, and U.S. Pat. No. 3,278,392 (enzymes), issued to Patchornik on Oct. 11, 1966. Although the above disclosures indicate the utility of the attached substances is not substantially impaired in the immobilization process, it has been found that, in many instances organic carrier materials have certain inherent disadvantages. For example, many organic carrier materials are subject to microbial attack, difficult to sterilize, difficult to comminute, and may not permit proper diffusion of reactants in certain environments. These and other disadvantages hve been overcome to a great extent by recent developments showing that inorganic materials can be used as carriers for the immobilized substances.

Antibodies, antigenic substances, and enzymes have been attached by covalent bonds to various inorganic materials through intermediate silane coupling agents as shown by U.S. Pat. No. 3,652,761 (antibodies and antigens), issued to H. H. Weetall on Mar. 28, 1972, U.S. Pat. No. 3,519,538 (enzymes), issued to R. A. Messing and H. H. Weetall on July 7, 1970, and U.S. Pat. No. 3,669,841 (enzymes),issued to R. E. Miller on June 11, 1972. In U.S. Pat. application Ser. No. 377,625, filed July 9, 1973 in the names of H. H. Weetall and S. Yaverbaum, and assigned to the present assignee, there is disclosed a method for extracting insulin from a solution which involves using a composite consisting of anti-insulin antibodies coupled to porous glass particles which, prior to coupling, had been surface activated with a cyanogen bromide solution. Various inorganics have also been used as sorbants in the RIA of substances such as thyroid hormones as shown by U.S. Pat. No. 3,666,854 (separating complexed hormone from free hormone by adsorbing the free hormone on various colloidal inorganics), issued on May 30, 1972 to A. M. Eisentraut, and U.S. Pat. No. 3,776,698 (using various inorganics to adsorb thyroid hormones after separation from a hormone-antibody complex), issued Dec. 4, 1973 to A. M. Eisentraut. A very recent article by W. F. Line et al. in Clin. Chem., 19, No. 12, pp. 1361–65 (1973) describes a SPRIA for digoxin substantially identical to one embodiment of our invention. See also an article by F. H. Bodley et al. in *Steroids*, Vol. 21, No. 1, pp. 1–16 (1973) wherein a similar SPRIA for progesterone is disclosed.

Although the above-cited U.S. Pat. No. 3,652,761 shows that various antibodies can be successfully coupled through intermediate silane coupling agents to a wide variety of inorganic materials, and that the resulting composites can be used to isolate the corresponding antigen from a solution, that patent broadly discloses the isolation of antigens using such composites. We have found that by making certain critical modifications of the broad teachings of U.S. Pat. No. 3,652,761, it is possible to prepare immunochemical composites which can be successfully used to provide an accurate and quick SPIRA for a number of substances in clinically significant concentration ranges. Our composites and the methods of using them in SPIRA are described in detail herein.

SUMMARY OF THE INVENTION

Our method of determining the concentration of a substance in a solution comprises the following steps:

A. incubating a solution of the substance with a known amount of radioactively labelled substance and a composite which is suspendable in the solution and consisting of antibodies to the substance which are coupled chemically through an intermediate silane coupling agent to an essentially water-insoluble, high surface area inorganic carrier, the incubation being for a time sufficient to form immunochemical complexes;

B. separating the complexes from the incubation solution;

C. determining the radioactivity of either the separated complexes or the remaining solution; and D. relating the determination of step (C) to a standard to determine the concentration of the substance. In preferred embodiments the inorganic carrier comprises essentially siliceous porous particles having an average particle size of between about 0.05 and 12 microns ($\mu$) and an average pore diameter of between about 30A and 1200A, the optimum average pore diameter within that range being sufficient to permit bonding of the antibodies and diffusion of the substance within the porous particles. Specific methods for determining concentrations of digoxin, insulin, and estriol are described.

SPECIFIC EMBODIMENTS

Our SPRIA is applicable to the measurement of concentrations of numerous substances for which specific antibodies exist. It should be pointed out that some of the substances need not even be per se antigenic since various substance-conjugates can be readily prepared which are antigenic and can induce the formation of antibodies to the substance. For example, some substances of relatively low molecular weight (e.g. the cardiac glycoside digoxin) will not necessarily induce formation of anti-digoxin antisera. However, when such a substance is combined with a material of higher molecular weight (e.g. a protein), it is possible to use such substance-conjugates to induce anti-substance antibodies. Thus, our method contemplates the SPRIA of a wide variety of substances which, alone or through modification, can be used to form specific anti-substance antibodies. Substance examples include digoxin, digitoxin, angiotensin I, angiotensin II, thyroxine, triiodothyronine, thyroid stimulating hormone, aldosterone, estriol, and other estrogens, insulin and like substances which commonly exist at very small concentrations. As used herein, the term substance refers to any compound or material for which there can exist specific antibodies.

As is common in conventional RIA, our SPIRA involves four basic steps: incubation, separation, counting, and relating the count to a standard. As used herein, the term incubating or its equivalent (e.g. incubation) refers to the step of providing a suitable environment which facilitates immunochemical complexation of a substance and an antibody. Such an environment includes those reaction conditions (e.g. pH, time, and temperature ranges, buffers, etc.) which are known or can be experimentally determined by one skilled in the art. The term separating, or its equivalent, refers to the step of removing the complexed products of incubation from the incubation solution. In SPRIA, this includes the removal of substantially all solid particles (e.g. carrier-antibodies composite plus complexed substances). Separation can be accomplished by simple centrifugation or other means. Counting refers to the step of determining the radioactivity of either the separated product or the remaining solution, commonly recorded as counts per minute (cpm). Relating the count or counts to a standard refers to the step of comparing a given count with means which will indicate a substance concentration vis-a-vis the given count. A very common method of using a count to determine the unknown concentration involves visually matching the count number with a concentration designation on a standard curve prepared with known amounts of labelled substance. Other methods of relating a determined count to unknown concentrations are possible (e.g. electronic).

We have found that certain physical and chemical characteristics are very critical for the inorganic carrier for the antibodies. Since our SPRIA must be useful for clinically significant concentration ranges of as low as sub-nanogram amounts per ml., the carrier must have a high surface area per gram to permit high loading of coupled antibodies through the silane coupling agents. As used herein, high surface area refers to inorganic materials having a surface area of at least about 10 m$^2$/g, preferably greater than about 25 m$^2$/g. The inorganic material must also be essentially water insoluble and have surface oxide or hydroxyl groups reactive with silane coupling agents. Such materials include various metal oxides such as $Al_2O_3$, $SiO_2$, $TiO_2$, $ZrO_2$, $Fe_3O_4$, and various porous glasses. For examples of various inorganic carriers to which silanes can be attached see U.S. Pat. No. 3,652,761.

To assure a high surface area and a suspendable composite of immobilized antibody, we prefer to use carriers that are porous and have a substantially uniform pore size distribution (e.g. the majority or the pore volume consisting of interconnected channels within about ±30% of the average pore or channel diameter). To assure a minimum surface area for antibody loading, the maximum average pore diameter should be no larger than about 1200A. The minimum average pore diameter must be large enough to permit diffusion and coupling of the antibody within the pores and to permit subsequent diffusion of substance within the pore. We have used porous carriers with average pore sizes as small as 30–40A. The optimum average pore size for a given antibody-carrier composite depends, however, on such factors as antibody and/or substrate size and diffusion and complexation times.

We have found that carrier particle size is very critical for the antibody-carrier composite of our method since to achieve a high degree of complexing sensitivity at a rapid rate, the composite must be suspendable in the incubation medium. As used herein, the term suspendable or suspension, when applied to either the inorganic carrier (porous or non-porous) or the resulting antibody-carrier composite formed therewith, refers to a carrier or composite having a particle size small enough to permit the composite to remain in suspension in the incubation medium without settling prior to complexation. It is essential to facilitate rapid assays that the composite remain in suspension during the incubation period so that maximum immunochemical complexation can occur in a given period of time (e.g. maximum diffusion of substance to immobilized antibody within the porous carrier particle). To assure maximum suspension of the composite during incubation (e.g. minimum of five minutes) we have found that the composite particle size should be closely controlled and that the average should be between about 0.05 and 12 microns, preferably less than about 4 microns. This composite particle size range is quite distinct from the range of immunochemical composite sizes disclosed in U.S. Pat. No. 3,652,761 and our extremely small particle size is essential for the rapid and sensitive SPRIA of substances in clinically significant concentration ranges as low as nanograms per milliliter. Particle sizes below 0.05 μ become difficult to centrifuge our and, hence, accuracy of assay results is affected. To assure suspendability of the ultimate composite, carrier particle size should not exceed about 12 μ.

In the examples below, we used representative inorganic carriers of commercially available particulate $SiO_2$, porous $SiO_2$, and porous glass. The porous $SiO_2$ consisted of micron-sized synthetic silica of uncontrolled porosity and was obtained from Grace Davison Chem. Co. of Baltimore, Maryland (Syloid 72—Lot No. 76568). The silica had a particle size distribution of 0.8 to 6 microns (diameter) with 50% of the particles 3.1 μ diameter. The porous glass was made by known methods. See, for example, the disclosure in U.S. Pat. No. 3,549,524 issued to Haller. The particulate $SiO_2$ was obtained from Cabot Corp. (Cab-O-Sil L-5) and had an average particle size of 0.05 μ. Controlled pore glasses (CPG) carriers having a range of average pore size from about 30A to about 1200A were used as indicated. Most of the porous glass samples used are commercially available. Samples of each pore size of glass were comminuted to average particle sizes between about 1 and 4 and 8–12 microns, as indicated.

The porous glass, particulate $SiO_2$, and porous $SiO_2$ carriers were silanized by known techniques. See, for example, U.S. Pat. No. 3,652,761 (carrier-silane-antibody) and U.S. Pat. No. 3,519,538 (carrier-silane-enzyme). The exact silanes and various modes of coupling antibody to the attached silanes are described in detail below.

In the examples below representative SPRIA techniques are described for determining clinically significant concentrations of digoxin, insulin, and estriol. The anti-digoxin antisera (goat) used to prepare the antibody-carrier composites was obtained from Biospheres, Inc. of Miami, Fl. and it had a titer of at least 1:50,000. The anti-insulin antisera was guinea pig anti-porcine serum obtained from Pentex (Lot No. 15). The anti-estriol antisera (1:10,000 titer) (sheep anti-estriol-$E_3$-serum) was obtained from a medical facility.

PREPARATION OF THE ANTIBODY-SILANE-CARRIER COMPOSITES:

The general techniques for reacting silanes with inorganics having available surface oxide or hydroxyl groups is disclosed in U.S. Pat. No. 3,652,761, and U.S. Pat. No. 3,519,538, both incorporated herein by reference. Once reacted with a silane coupling agent, the carrier is referred to as silanized and the carrier surface will then consist of organic groups which are indicative of the starting material silane. The organic surface groups can be, and often are, further modified to form reactive groups desired for a given coupling technique with the antibody. It is important that the active or complexing site on a given antibody does not take part in the coupling procedure since that site must remain free for complexing after the antibody has been immobilized through the silane. Thus, in silanizing an inorganic carrier, care must be taken in choosing an appropriate reactive group for the silane residue on the silanized carrier. In our examples, the silanized carriers had alkylamine or arylamine surface groups, as indicated. The alkylamine surface was prepared by reacting the inorganic carrier with γ-aminopropyltriethoxysilane (Union Carbide A-1100), giving an aminopropyl surface. The arylamine surface was prepared by first reacting the aminopropyl surface with p-nitrobenzoal chloride and triethylamine in chloroform to form an arylnitrate which was then reduced in an aqueous sodium dithionite solution at 100°C. to form p-aminobenzyl propyl surface groups. As used herein, the terms alkylamine and arylamine refer to surface derivatives of silanized carriers having such respective groups. The choice of either group for a given silanized carrier vis-a-vis the antibody to be coupled will depend on the coupling method used. In our illustrative examples, we used a Schiff-Base reaction to couple antibody to alkylamine-carrier, an azo reaction to couple antibody to arylamine-carrier, and a thiourea reaction to couple antibody to both alkylamine and arylamine carriers. Specific directions for preparing each composite of antibody-silanecarrier are given below with indicated characteristics of each carrier material used.

EXAMPLE I (Preparation and Use of Anti-Digoxin-Silane-Carrier)

The goat anti-digoxin serum was chemically coupled to alkylamine and/or arylamine surface derivatized porous glass particles by three methods. In each case, 100 mg of antiserum protein was offered to 1 gram dry weight of the silanized glass particles, the physical characteristics of the various glass samples being summarized in Table I following the coupling descriptions:

A. The procedure for diazotization of arylamine glass was performed at 0°C. to about 10°C. by first adding 5 ml. of 2N HCl to the glass. A 0.25 g portion of solid $NaNO_2$ was added next. The reaction mixture was placed in a desiccator and aspirated during diazotization for 30–40 minutes. The diazotized glass was removed from the desiccator and washed by centrifugation four times with ice cold water. The diazotized glass derivative was added to the antiserum (which had been previously placed in an ice bath and adjusted to pH 8.0–8.5). The glass-antiserum mixture was continuously stirred with a magnetic flea or manually and the pH maintained with 0.1N NaOH. The reaction was monitored until no drop in pH was observed over a 30-minute period (usually 1–2 hours). At this point an optional 0.25ml. of 1M glycine solution in borate buffered saline (BBS, 0.01M, pH 8.5 ±0.1) can be added with stirring, and the mixture placed in the refrigerator overnight, or returned to the refrigerator for several hours, as required. The reaction mixture was washed by centrifugation four times with cold (e.g. about 5°–10°C.) BBS and stored as a wet cake in the refrigerator.

B. Schiff-Bass coupling with glutaraldehyde was initiated at room temperature. Enough 2.5% glutaraldehyde solution (i.e., 25% glutaraldehyde diluted 1:10 in 0.1M sodium phosphate buffer, pH 7.0) was added to cover 1 g of alkylamine glass particles. The reaction mixture was placed in a desiccator jar attached to an aspirator for 60 minutes. The product was removed and washed four times by centrifugation with large volumes (e.g. about 45 ml.) of distilled water. Increments (e.g. about 50–100 mg) of the product were added to antiserum (previously adjusted to pH 7.0) in an ice bath, using as little liquid as possible. The reaction was continued for at least 2 hours. The composite was washed three times with cold distilled water and once with cold BBS and the wet cake stored in the refrigerator (4°–5°C.).

C. The thiourea derivative was prepared by adding 100 ml. of 1% (by weight) thiophosgene in $CHCl_3$ to 1 g of glass and refluxed for at least 2½ to 3 hours. The product was washed with $CHCl_3$, quickly air-dried and placed in a vacuum desiccator overnight. The isothiocyanate CPG derivative was added to antiserum previously adjusted to pH 9 at room temperature. The pH was maintained between pH 8.5–9.2 using 0.1N NaOH. The reaction was first agitated in an aspirator for 30 minutes and then continued for an additional 2 hours, all at room temperature. The product was washed with distilled water and stored as a wet cake in the refrigerator (4°–5°C.).

Table I summarizes the average amount of anti-digoxin anti-serum protein we were able to bind to one gram quantities of indicated porous glass particles by the coupling methods described above.

TABLE I

| Porous Glass Properties | | (mg protein/g porous glass) Coupling Method | | |
|---|---|---|---|---|
| Pore Size (A) | Particle Size ($\mu$) | Azo | Schiffs-Base | Thiourea |
| 35 | 1–4 | 11.5 | — | — |
|  | 8–12 | — | — | — |
| 150 | 1–4 | 64.9 | 45.9 | 58.9 |
|  | 8–12 | 41.2 | — | — |
| 390 | 1–4 | 86.3 | 55.8 | 61.9 |
|  | 8–12 | 78.6 | 55.4 | 67.7 |
| 555 | 1–4 | 74.6 | 58.4 | 82.8 |
|  | 8–12 | 68.8 | 60.9 | 98.1 |
| 685 | 1–4 | 41.5 | 55.9 | 59.7 |
|  | 8–12 | — | — | — |
| 1150 | 1–4 | 38.3 | 36.8 | 51.2 |
|  | 8–12 | 43.8 | 45.3 | 53.5 |
| 1200 | 1–4 | 41.3 | 38.3 | 54.0 |
|  | 8–12 | — | — | — |

The highest loading of antiserum was on CPG particles having an average pore diameter within the range of 390A to about 685A, although the composite having a CPG carrier with an average pore diameter in the 1000A to 1200A were shown to have useful biological activity.

Figures 1, 2, 3:
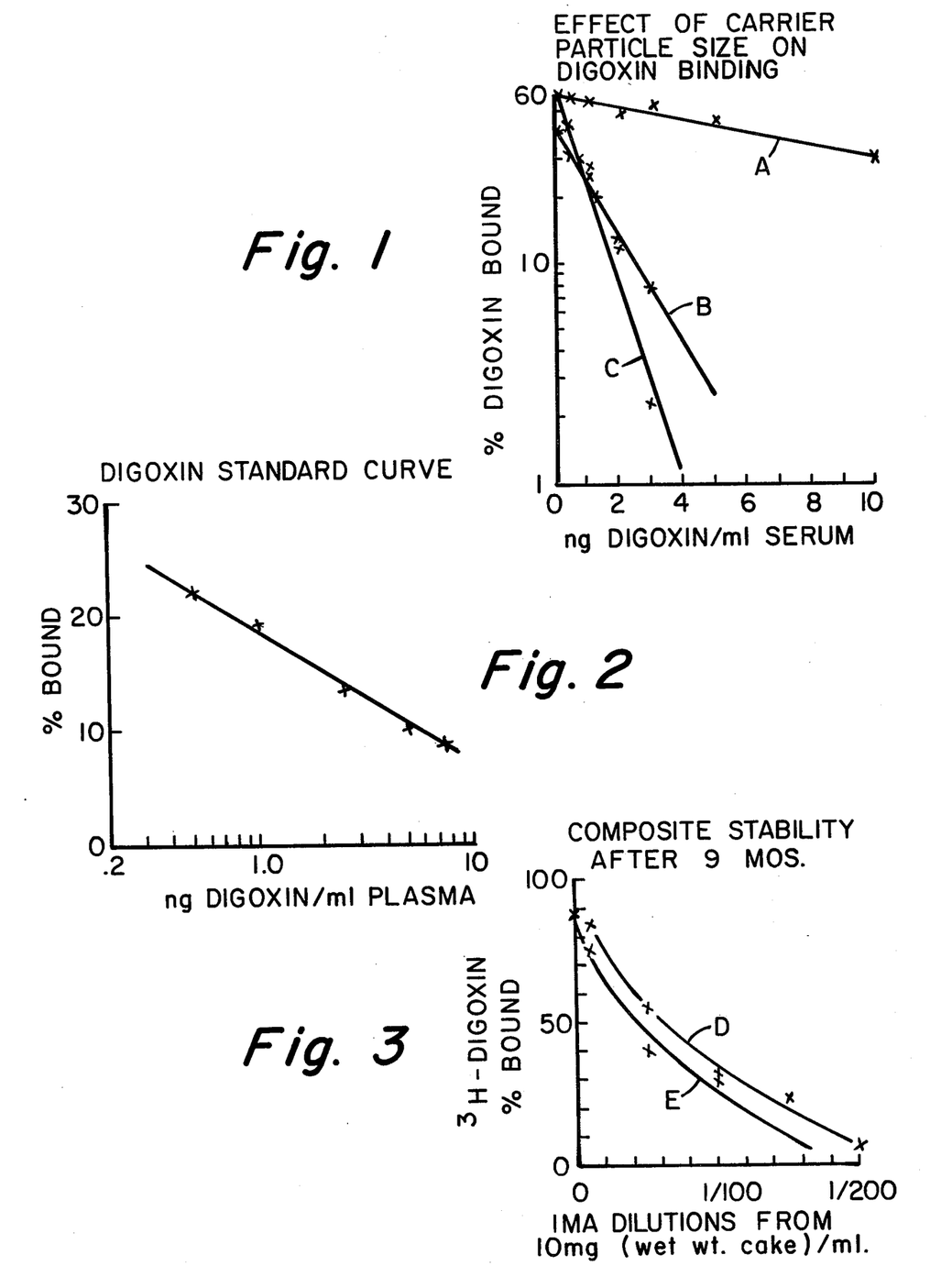
FIG. 1 compares the effects of varying carrier particle size on digoxin binding sensitivity in the clinically significant concentration range for digoxin.
FIG. 2 is a typical standard curve for the SPRIA of digoxin.
FIG. 3 is a curve showing binding ability of an IMA at various dilutions.

FIG. 1 illustrates comparative SPRIA displacement curves generated using immobilized anti-digoxin antibodies on porous glass carriers having three different average particle sizes. In all cases, the porous glass particles had an average pore size of about 555A. Curve A was generated using an IMA (azo coupled) carrier of 30 $\mu$ average particle size and 200 $\mu$g (wet weight) IMA. Curve B was generated using a 10 $\mu$ porous glass carrier (26.7 $\mu$g, wet weight) and curve C was generated using a IMA having a carrier particle size of about 2 $\mu$ (26.7 $\mu$g, wet weight). As can be seen from FIG. 1, the 30 $\mu$ carrier did not produce a useful assay curve whereas the 2 $\mu$ and 10 $\mu$ carrier did. In all three samples, a 1% wet weight suspension was used, diluted 1:50 for curve A and 1:375 for curves B and C. The indicated dilutions were chosen to show digoxin binding curves within the significant concentration range.

Standard curves for digoxin determinations were prepared with the composites. A typical standard curve using a composite consisting of the anti-digoxin antiserum coupled via the azo method to porous glass particles having an average pore size of about 555A and average particle size of about 1 $\mu$ is shown in FIG. 2. Tritiated ($^3H$) digoxin obtained from New England Nuclear Corp. was used to assay known concentrations of digoxin using the standard curve of FIG. 2. The incubation time was for ten minutes in each assay. The results are summarized in Table II. With the exception of the outlier, the results show good agreement. Average error including the outlier was +3.55% and without the outlier, +0.86%. The simulated assay indicated the SPRIA using the defined CPG particles were rapid (e.g., about ten minutes), sensitive in the clinically significant range for digoxin (e.g., 0.2 to 10 ng/ml.), reproducible, and easy to perform.

The importance of having a carrier particle size which is suspendable is illustrated in FIG. 1. There, the use of the composite having the 30 $\mu$ carrier particle size, as shown, did not result in a useful assay curve for clinically significant digoxin concentrations whereas suspendable particles of 10 and 1 $\mu$ average carrier size were useful.

TABLE II

Recovery of Known Amounts of Digoxin From Serum Samples
ng Digoxin/ml. Serum

| Added | Found | Expected | Percent Difference |
|---|---|---|---|
| 0 | 3.70 |  |  |
|  | 3.60 |  |  |
| 0.50 | 4.35 | 4.20 | +3.50 |
|  | 4.10 |  | −2.30 |
| 1.00 | 5.50 | 4.70 | +17.00 |
|  | 5.00 |  | +6.30 |
| 2.50 | 6.00 | 6.20 | −3.20 |
|  | 6.20 |  | 0.0 |

ANTI-DIGOXIN ANTISERA COUPLED TO POROUS SILICA:

The anti-digoxin antisera was also coupled successfully to porous silica particles having a particle size distribution of 0.8 to 8 $\mu$ (diameter) with 50% of the particles 3.7 $\mu$ diameter. An arylamine surface was prepared (as described above for CPG on a one gram sample of the $SiO_2$ (Syloid 72). The arylamine silica was then diazotized (as above) and added in increments of about 50 to 100 mg to a 1.3 ml. quantity of the anti-digoxin antiserum containing 82 mg total protein. A pH of 7.5–8.5 was maintained with 0.1N NaOH and the mixture was reacted for 24 hours at about 5°C., and washed four times with filtered distilled water (FDW). A ten mg. (wet weight)/ml. suspension of the immobilized antiserum (IMA) in FDW was assayed for bound protein and biologic activity.

A ninhydrin protein determination indicated 80.7 mg protein/gram of silica or 97% of the antiserum offered being bound. An initial assay of biological activity of the composite (curve D) and a subsequent assay (curve E) of the same composite prepared nine months later are compared in FIG. 3. A maximum of 15% of the IMA activity had been lost for equivalent dilutions during that period, thus indicating excellent stability of the composite (stored as a wet cake at 5°C.).

percent of bound insulin. The results are summarized in Table III.

TABLE III

| Carrier and Particle Size | Immobilized Composite mg Protein/g* Dry Weight of Particles | % Protein Coupled+ | Biological Activity IMA Protein μg× | [125]I-Insulin Bound, %ɛ |
|---|---|---|---|---|
| Guinea Pig Anti-Porcine Insulin Serum | | | 0.40 | 56.7[1] |
| 1 μ CPG | 24.6 | 96.5 | 0.45 | 54.1 |
| 12 μ CPG | 22.8 | 90.0 | 0.71 | 50.5 |
| silica (4 μ) | 27.6 | 108.2 | — | — |
| silica (0.05 μ) | 26.4 | 103.5 | 0.81 | 57.9 |
| Bovine Serum Albumin | | | 0.40 | 0[1] |
| 1 μ CPG | 20.4 | 80.0 | 0.378 | 0 |
| 12 μ CPG | 21.7 | 85.0 | 0.65 | 0 |
| silica (4 μ) | 25.6 | 100.5 | 4.02 | 0 |
| silica (0.05 μ) | 9.1 | 50.6 | 0.222 | 0 |

*Protein determined by ninhydrin method.
+25.50 mg antiserum or BSA offered per gram glass.
×Protein concentration of IMA at optimal dilution for SPRIA or DCC[1] method.
ɛ0.2 ng [125]I-Insulin Tracer.

EXAMPLE II (Preparation and Use of Anti-Insulin-Silane-Carrier)

The guinea pig anti-porcine insulin serum was coupled chemically through silane coupling agents to silica particles of 0.05 μ average particle size, porous glass particles of 1.0 and 12.0 μ average particle sizes, each having an average pore diameter of about 550A, and silica particles having an average particle size of 4.0 μ. Portions of each of the four carrier materials were silanized as above to form alkylamine and then arylamine derivatives, as described above for the anti-digoxin composite preparation. Both anti-insulin antiserum and bovine serum albumin (BSA) were separately coupled to each of the carriers to compare the couplings of two different proteins. One gram samples of each of the arylamine carriers were diazotized and these were added to individual tubes containing 1 ml. of antiserum or 1 ml. of BSA and the coupling reaction was continued for (at a maintained pH of 8.5) two hours and periodically tested for diazonium sites with a 0.1% beta-naphthol solution. When the pH had steadied at 8.5, the reactants were refrigerated overnight.

The immobilized anti-insulin preparations were analyzed at 4 week intervals for 24 weeks and found to be stable when stored as wet cakes and heavy slurries at 5°C. Storage stability data indicated a minimum half life protein stability to be about 3.2 years. The half life for biological activity (complexing ability) was found to be about 2 years.

Figure 4:
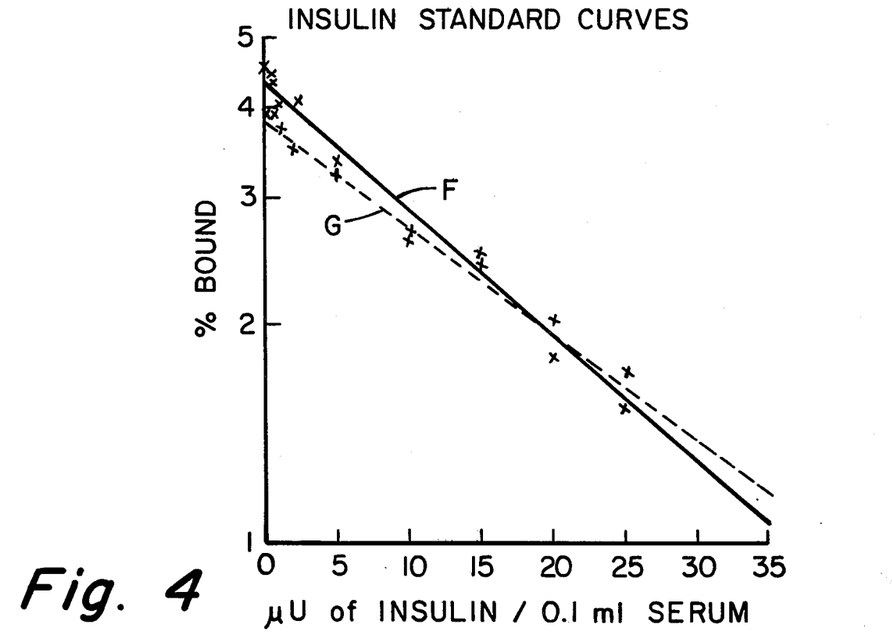
FIG. 4 shows typical standard curves for the SPRIA of insulin.

STANDARD CURVE:

Standard curves were prepared for each sample by diluting each suspension so that each test tube contained 1 μg (dry weight) of immobilized anti-insulin antiserum. A representative standard curve using anti-insulin antiserum coupled to the porous glass particles (1 μ) is shown as FIG. 4. These curves were used to assay known amounts of insulin added to pooled normal rabbit serum. Known amounts of insulin from 0–25 μU were added to 0.1 ml. of rabbit serum (0–250 μU/ml.). Two of these assays are summarized in Table IV. The rabbit serum had an average insulin concentration (without added insulin) of 4.67 μU/ml. The final average estimate of insulin agreed to within 99% in the first experiment and 96% in the second experiment.

TABLE IV

Solid Phase Radioimmunoassay of Insulin in Pooled Normal Rabbit Sera Using 1μ CPG Anti-Insulin Immunoadsorbent at 25°C. for 2 hours

| | Experiment 1* | | | | Experiment 2* | | | |
|---|---|---|---|---|---|---|---|---|
| μU Insulin Added Per 0.1 ml. Sample | μU Insulin Expected | μU Insulin Estimated | % Error | μU Insulin× Calculated Per 0.1 ml. Serum | μU Insulin Expected | μU Insulin Estimated | % Error | μU Insulin No. Calculated Per 0.1 ml. Serum |
| 0 | — | 4.67 | — | 4.67 | — | 4.78 | — | 4.78 |
| 5 | 9.67 | 7.20 | −25.5 | 2.20 | 9.78 | 10.00 | +2.2 | 5.00 |
| 10 | 14.67 | 16.00 | +9.0 | 6.00 | 14.78 | — | — | — |
| 15 | 19.67 | 21.00 | +6.7 | 6.00 | 19.78 | 19.00 | −4.0 | 4.00 |
| 25 | 29.67 | — | — | — | 29.78 | 31.00 | +4.0 | 6.00 |
| average | — | — | 13.7 | 4.73 | — | — | 3.4 | 5.00 |

*Duplicate Samples.
×Expected Value = 4.67.
No. Expected Value = 4.78.

The immobilized anti-insulin antiserum (IMA) was then washed with 0.01M borate buffered silane (BBS), pH 8.5, and stored at 5°C. as a wet cake or heavy slurry (0.8 g wet weight/7 ml. buffer) in stoppered tubes.

All samples were then analyzed for amount of protein coupled per gram of carrier, and the biological activity of the immobilized anti-insulin was determined by adding 0.2 ng of $^{125}$I insulin tracer to each tube containing graduated concentrations of IMA and determining the

EXAMPLE III (Preparation and Use of Anti-Estriol-Silane-Carrier)

The immobilized antiserum was prepared as follows: The sheep anti-estriol ($E_3$) serum was chemically coupled to an arylamine derivative of 96% silica controlled pore glass (CPG). The original average porosity of the CPG was 550A before reduction of the particle size from an average 40/80 mesh to an average of 1 micron (μ). The 1 μ CPG was derivatized to arylamine as described above. One gram dry weight of 1 μ arylamine CPG was diazotized in an ice bath by acidification with 10 ml. of 2N HCl followed by 0.25 g of solid NaNO₂. The iced mixture was stirred and transferred to a vacuum desiccator and aspirated for 20 to 40 minutes. The diazotized glass derivative was washed several times by centrifugation at 5°C. and 10,000 rpm for 30 minutes with cold distilled water. The cold, washed diazonium glass was added in increments of 50–100 mg to 1 ml. of sheep anti-E₃ in a small beaker containing a magnetic flea seated in an ice bath. The antiserum was previously adjusted to pH 8.0–8.5 with buffer or 0.1N NaOH before addition of the diazotized glass derivative. The reaction mixture was constantly stirred and the pH maintained during and after addition of the diazotized glass. The pH levelled off after 120 minutes and the reaction vessel was covered and placed in a 4°C. refrigerator overnight. The immobilized antiserum preparation was thoroughly washed several times with cold phosphate buffer (0.01M, pH 7.4) containing 0.9% NaCl (PBS) and centrifuged at 4500 rpm and 5°C. for 30 minutes several times, then stored as a slurry in 3 ml. of PBS containing 0.02% NaN₃ in a refrigerator at 4°C. until used.

Figure 5:
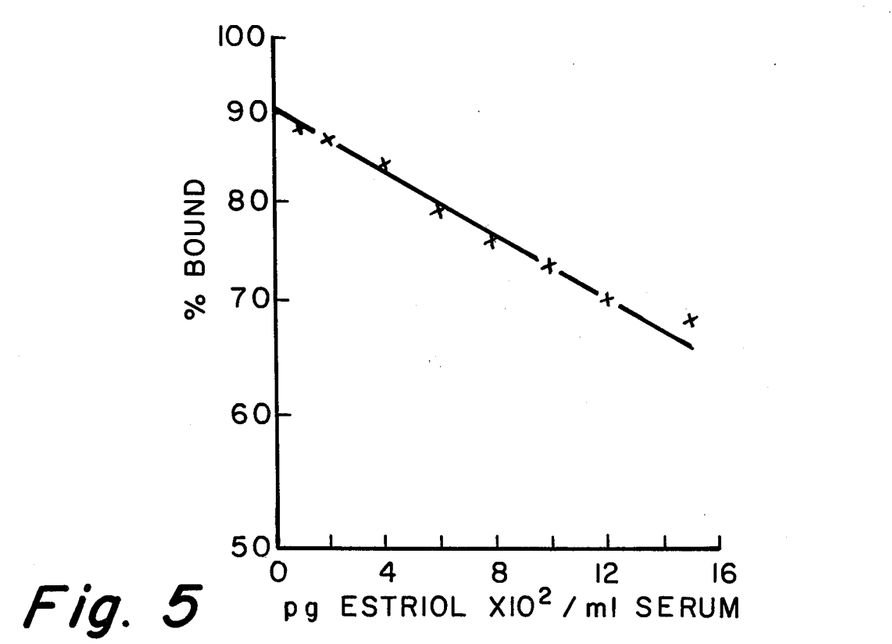
FIG. 5 is a typical standard curve for the SPRIA of estriol.

Standard curves were obtained by first determining the dilution or concentration of immobilized antiserum that would bind 50 to 80% of 14.4 pg of ³H-estriol containing 10 nc of radioactivity [New England Nuclear, Estriol-6.7, ³H (N)] and a gradient of unlabelled E₃ from 0 up to 1500 pg. A duplicate series of glass tubes (10 × 75 mm) were charged with 0.2 ml. of ethanol containing 15,000 cpm ³H₃ (14 pg). Then these tubes were charged with 0, 100, 200, 400, 600, 800, 1000, 1200, or 1500 pg of E₃ in 0.2 ml. ethanol. The alcohol solvent was evaporated in a vacuum oven. The immobilized antibody suspension (1 gram/4 ±1 ml. PBS) was diluted 1:500 in PBS, and constantly agitated with a magnetic stirrer in an ice-water bath to achieve a homogeneous suspension. A volume of 0.4 ml. of the suspension was added to each tube. The tubes were stirred thoroughly on a vortex mixer and incubated in icewater for 30 minutes. The stirring was repeated at 10 minute intervals. The tubes were centrifuged after 30 minutes at 5°C. and 3500 rpm for 15 minutes. An aliquot of 0.2 ml. of the supernatant fluid was transferred to a liquid scintillation counting vial containing 10 ml. of Insta-Gel for tritium assay. The results are shown in Table V and FIG. 5.

TABLE V

| Estriol pg | Estriol Standard Curve Average CPM* | Percent Free |
|---|---|---|
| ³M-Estriol | 15,000 | |
| 0 | 1,450 | 19.3 |
| 100 | 1,765 | 23.5 |
| 200 | 1,975 | 26.3 |
| 400 | 2,435 | 32.5 |
| 600 | 3,110 | 41.4 |
| 800 | 3,625 | 48.3 |

TABLE V-continued

| Estriol pg | Estriol Standard Curve Average CPM* | Percent Free |
|---|---|---|
| 1000 | 4,035 | 53.8 |
| 1200 | 4,500 | 60.0 |
| 1500 | 4,840 | 64.6 |

*Delta of two samples.

The reproducibility of the standard curve and the recovery of test samples were demonstrated in the following manner. Two concentrations of 5000 pg per milliliter of ethanol were prepared. Aliquots of 0.1 and 0.2 ml. of the alcohol solution in triplicate were assayed against a standard curve. The results are shown in Table VI.

TABLE VI

Recovery of Estriol From "Unknown" Sample

| Estriol Sample ml. | Average cpm | Estriol Recovered pg | Percent Recovered |
|---|---|---|---|
| Sample No. 1 | | | |
| 0.1 | 3093 | 480 | 96.0 |
| 0.2 | 4523 | 970 | 97.0 |
| Sample No. 2 | | | |
| 0.1 | 3280 | 555 | 111.0 |
| 0.2 | 4540 | 990 | 99.0 |

The above illustrative examples indicate that quick, accurate, and sensitive SPRIAs are possible when the appropriate antibody is chemically coupled silane coupling agents to high surface area, essentially water insoluble inorganic carrier materials having a particle size between about 0.05 μ and about 12 μ. Since the methods disclosed herein are subject to various modifications, it is intended that the scope of the disclosed invention should be limited only by the appended claims.

We claim:

1. A method for determining the concentration of digoxin in a solution which comprises the steps of:
   a. incubating the solution with a known amount of radioactively labelled digoxin and a suspendable composite consisting of anti-digoxin antiserum coupled chemically through an intermediate silane coupling agent to a high surface area essentially water-insoluble inorganic carrier having an average particle size between about 0.05 and 12 microns, the incubation being for a period sufficient to form immunochemical complexes;
   b. centrifuging the complexes from the solution;
   c. counting the radioactivity of either the centrifuged complexes or the remaining solution; and
   d. relating the count of step (c) to a standard to determine the concentration of digoxin.

2. The method of claim 1 wherein the incubation of step (a) is for at least 10 minutes.

3. The method of claim 2 wherein the inorganic carrier is porous and selected from the group consisting of porous glass particles and porous silica particles.

4. The method of claim 3 wherein the average pore diameter of the porous particles is between about 350A and about 1200A.

5. A method for determining the concentration of insulin in a solution which comprises the steps of:
   a. incubating the solution with a known amount of radioactively labelled insulin and a suspendable composite consisting of anti-insulin antibodies coupled chemically through a silane coupling agent to a high surface area, essentially water insoluble inorganic carrier having an average particle size between about 0.05 and about 12 microns, the incubation being for a period sufficient to form immunochemical complexes;

b. separating the complexes from the solution;
c. counting the radioactivity of either the separated complexes or the remaining solution; and
d. relating the count of step (c) to a standard to determine the concentration of insulin.

6. The method of claim 5 wherein the inorganic carrier is porous and selected from the group consisting of porous glass particles and porous silica particles.

7. A method for determining the concentration of estriol in a solution which comprises the steps of:
  a. incubating the solution with a known amount of radioactively labelled estriol and a suspendable composite consisting of anti-estriol antibodies coupled chemically through an intermediate silane coupling agent to a high surface area, essentially water-insoluble inorganic carrier having an average particle size between about 0.05 and about 12 microns, the incubation being for a period sufficient to form immunochemical complexes;
  b. separating the complexes from the solution;
  c. counting the radioactivity of either the separated complexes or the remaining solution; and
  d. relating the count of step (c) to a standard to determine the concentration of estriol.

8. The method of claim 7 wherein the particles are porous.

9. The method of claim 8 wherein the particles consist of porous glass.

* * * * *

UNITED STATES PATENT AND TRADEMARK OFFICE
CERTIFICATE OF CORRECTION

PATENT NO. : 3,975,511
DATED : August 17, 1976
INVENTOR(S) : William P. Vann and Sidney Yaverbaum It is certified that error appears in the above-identified patent and that said Letters Patent are hereby corrected as shown below:

Column 4, line 62, after "average" insert -- size --.

Column 5, line 14, " 3.1" should be -- $\geq 3.1$ --.

Column 6, line 15, "body-silanecarrier" should be -- body-silane-carrier --.

Column 6, line 68, "1%" should be -- 10% --.

Column 8, line 50, " 3.7" should be -- $\geq 3.7$ --.

Column 10, line 31, "1 µg" should be -- 10 µg --.

Column 11, line 53, "icewater" should be -- ice-water --.

Signed and Sealed this

Ninth Day of November 1976

[SEAL]

Attest:

RUTH C. MASON
*Attesting Officer*

C. MARSHALL DANN
*Commissioner of Patents and Trademarks*